United States Patent [19]

Edenbaum

[11] Patent Number: 5,445,599
[45] Date of Patent: Aug. 29, 1995

[54] WARP-KNIT CASTING BANDAGE FABRIC, WARP-KNIT CASTING BANDAGE AND METHOD FOR MAKING BANDAGE

[75] Inventor: Martin Edenbaum, Princeton Junction, N.J.

[73] Assignee: Carapace, Inc., Broken Arrow, Okla.

[21] Appl. No.: 98,535

[22] Filed: Jul. 28, 1993

[51] Int. Cl.[6] ............................................. B32B 7/00
[52] U.S. Cl. ................................. 602/76; 66/192; 66/195; 66/202; 156/88; 156/148; 156/250; 156/272.2; 428/228; 428/229; 428/253; 428/254; 428/296; 428/193; 602/75; 602/900
[58] Field of Search .............. 602/75, 76, 900; 66/192, 195, 202; 428/253, 254, 193, 296, 228, 229; 156/88, 148, 250, 272.2

[56] References Cited

U.S. PATENT DOCUMENTS

| | | | |
|---|---|---|---|
| 4,323,061 | 4/1982 | Usukura | 128/90 |
| 4,733,545 | 3/1988 | Weinle et al. | 66/202 |
| 4,745,912 | 5/1988 | McMurray | 128/90 |
| 4,748,078 | 5/1988 | Doi et al. | 428/245 |
| 4,818,316 | 4/1989 | Weinle et al. | 156/88 |

*Primary Examiner*—James J. Bell
*Attorney, Agent, or Firm*—Panitch Schwarze Jacobs & Nadel

[57] ABSTRACT

A warp-knit casting bandage fabric is provided which comprises a first group of a plurality of individual continuous multifilament fiberglass yarns which form lengthwise extending chains of spaced-apart loops and a second group of a plurality of individual continuous multifilament fiberglass yarns which are separately interspersed with a plurality of individual continuous thermoplastic yarns forming a widthwise extending and lengthwise spaced-apart inlay which is interlaced with the spaced-apart loops forming an open-knit construction wherein the continuous thermoplastic yarns comprise from about 50% to about 100% of the total number of individual yarns forming the inlay. An elongated, resin-impregnated bandage, having a leading edge and a trailing edge, made from the warp-knit casting bandage fabric is also provided as well as a method for forming such resin-impregnated bandages.

17 Claims, 2 Drawing Sheets

WARP-KNIT CASTING BANDAGE FABRIC, WARP-KNIT CASTING BANDAGE AND METHOD FOR MAKING BANDAGE

FIELD OF THE INVENTION

The present invention relates to a warp-knit casting bandage fabric, a warp-knit casting bandage made from that fabric and a method for making warp-knit casting bandages.

BACKGROUND OF THE INVENTION

Orthopedic casts are typically formed by placing a protective sleeve over a body member and wrapping the protective sleeve with padding to cushion the body member. Once the padding is in place, a roll of flexible, warp-knit fiberglass fabric webbing impregnated with water-activated casting material is wet with water, unrolled and wrapped around the body member. The casting material then sets and hardens forming a cast.

Warp-knit fiberglass is used in casting bandages due to its strength and flexibility. Such fabrics are knit in long lengths and cut into individual casting bandages. Problems arise from use of glass fiber, however, with respect to the tendency of the glass fiber to unravel and fray, particularly on the leading and trailing edges of the elongated fabric.

Initial solutions to the fraying problem proposed in the art include methods involving heat cleaning of the fiberglass to remove starch finish on the fiberglass yarn prior to impregnating the bandage with the water-activated casting material. This method, while providing a tighter fabric having less tendency to fray, adversely affects the ability of the fiberglass to stretch.

Subsequently, it was proposed that a non-heat cleaned fiberglass fabric which has a water-activated resin impregnated casting material compatible with the starch finish on the fiberglass yarn could be used. A two-bar, warp-knit fabric of acceptable stretch character made of non-heat cleaned fiberglass having such a compatible resin was developed and has been successfully marketed under the trademark K-Cast by the Kirschner Medical Corporation of Timonium, Md. These non-heat treated bandages, while preserving the fiberglass stretch characteristics, still have a tendency to unravel and fray.

A further proposed solution to the fraying problem is the use of warp-knit polyester fabric. While such a fabric reduces fraying, it lacks the desirable characteristics of fiberglass.

More recently, U.S. Pat. No. 4,745,912 which is herein incorporated by reference, proposes the addition of a dual fiberglass/thermoplastic fill yarn provided by a back beam to a non-heat treated fiberglass warp yarn to form a fabric which is subjected to heat bonding in order to prevent fraying. This fabric due to its density, however, decreases the flexibility of the fabric.

Therefore, there is a need in the art for a fiberglass warp-knit fabric which does not unravel and fray, but which still retains all the favorable characteristics of a fiberglass fabric casting bandage.

SUMMARY OF THE INVENTION

The warp-knit casting bandage fabric according to the present invention comprises a first group of a plurality of individual continuous multifilament fiberglass yarns which form lengthwise extending chains (warp yarns) of spaced-apart loops, and a second group of a plurality of individual continuous multifilament fiberglass yarns which are separately interspersed with a plurality of individual continuous thermoplastic yarns forming a widthwise extending and lengthwise spaced-apart inlay (weft or fill yarns). The inlay is interlaced with the lengthwise extending chains of spaced-apart loops creating an open-knit construction. The continuous thermoplastic yarns comprise from about 50% to about 100% of the total number of individual yarns forming the inlay. Preferably, the inlay is comprised of a ratio of two continuous thermoplastic yarns to one continuous multifilament fiberglass yarn.

The elongated, resin-impregnated, warp-knit casting bandage, made from the fabric of the present invention, comprises a leading edge and a trailing edge. The leading edge is formed by cutting a continuous length of the warp-knit casting bandage fabric, impregnated with resin, in a direction transverse to the longitudinal axis of the bandage at a first position on the continuous length at which the continuous thermoplastic yarns of the fabric are bonded to the widthwise and lengthwise extending continuous multifilament fiberglass yarns. The trailing edge is formed by cutting the same continuous length of fabric in a transverse direction (generally parallel to the first cut) at a second position, spaced apart lengthwise from the first position, at which the continuous thermoplastic yarns are bonded to the widthwise and lengthwise extending continuous multifilament fiberglass yarns.

The method for making the elongated, warp-knit casting bandage of the present invention comprises forming a bond between the thermoplastic yarns and the lengthwise and widthwise extending fiberglass yarns within the fabric of the present invention by softening or melting the thermoplastic yarns, for example, by application of heat or ultrasonic energy, and cutting the fabric in a direction transverse to the longitudinal axis of the fabric at a first position forming a leading edge and at a second position forming a trailing edge.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment of the warp-knit casting fabric which is presently preferred. It should be understood, however, that the invention is not limited to the precise arrangement shown. In the drawings.

In the drawings, like numerals are used to indicate like elements throughout.

DETAILED DESCRIPTION OF PREFERRED EMBODIMENTS

This invention concerns a warp-knit casting bandage fabric 9 for use primarily in preparing resin-impregnated orthopedic casts. While described herein as a fabric 9 useful for forming casts, use of such fabric 9 is not so limited. It will be understood by those skilled in the art that such fabric 9 may also be used as a base fabric for a splint, for use as a mold for a prosthetic device or other similar orthopedic uses. The fabric 9 may be made on a single needle bar warp knitting machine and may be characterized as a single needle, two-bar warp-knit fabric. The fabric 9 may be made, for example, in the manner described in U.S. Pat. No. 4,745,912 with the exception that only two beams are required for knitting the fabric 9 as distinguished from the three beam construction described therein.

Figure 1:
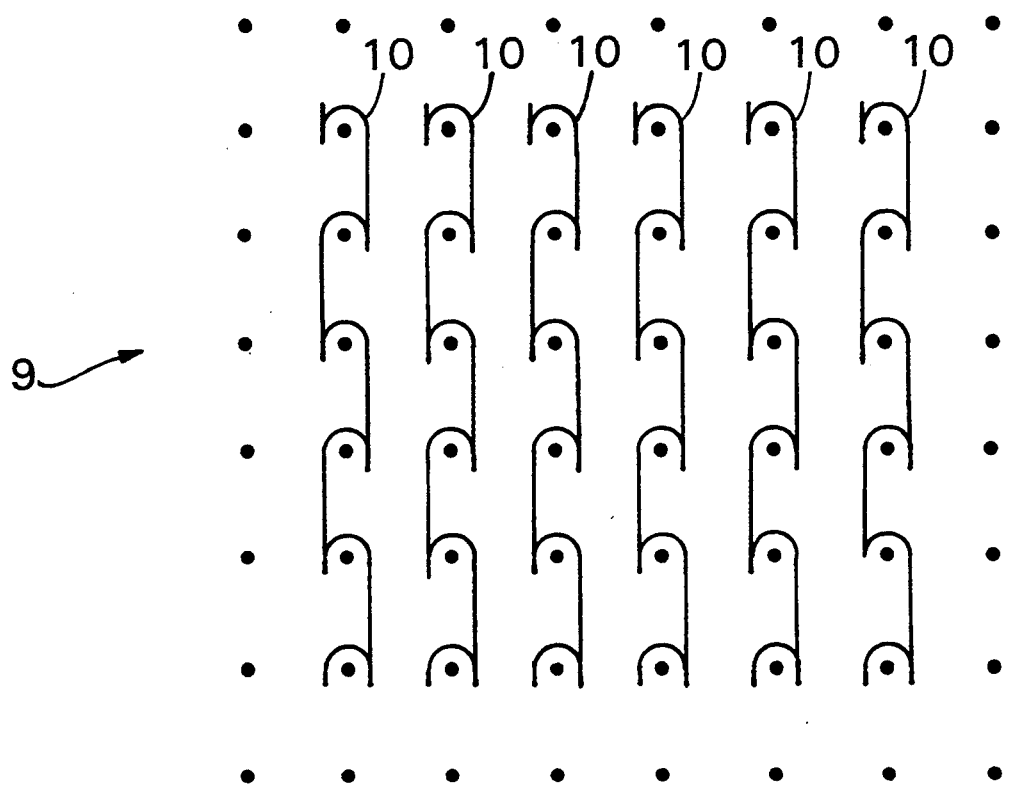
FIG. 1 is a stitch diagram for the first guide bar forming a chain stitch with continuous multifilament fiberglass yarns.

As shown in FIG. 1, the fabric 9 comprises a first group of a plurality of individual continuous multifilament fiberglass yarns 10 forming lengthwise extending chains of spaced-apart loops. The fiberglass yarns 10 are preferably those having one turn per inch in the Z direction as used in standard terminology. The diameter of the fiberglass yarns 10 should be from about 0.00015 inches to about 0.00036 inches, preferably about 0.00025 inches. In addition, the strand count should be from about 37 to about 150, preferably 100.

Figure 2:
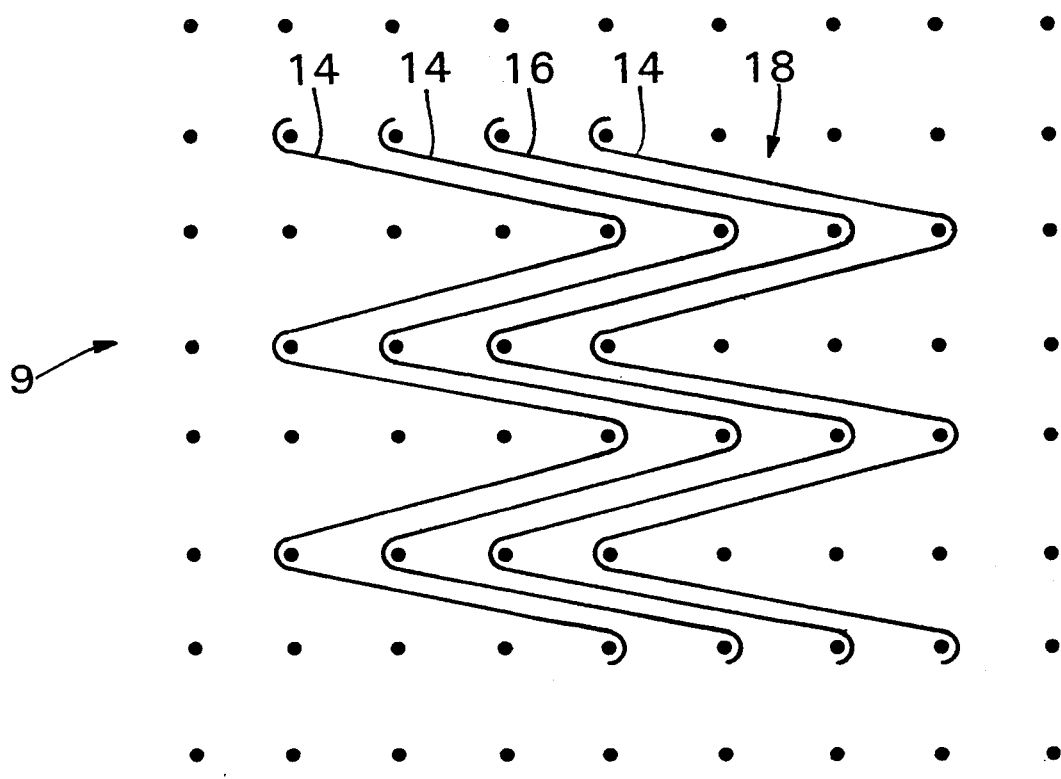
FIG. 2 is a stitch diagram for the second guide bar forming the inlay of continuous multifilament fiberglass yarns and continuous thermoplastic yarns.
Figure 3:
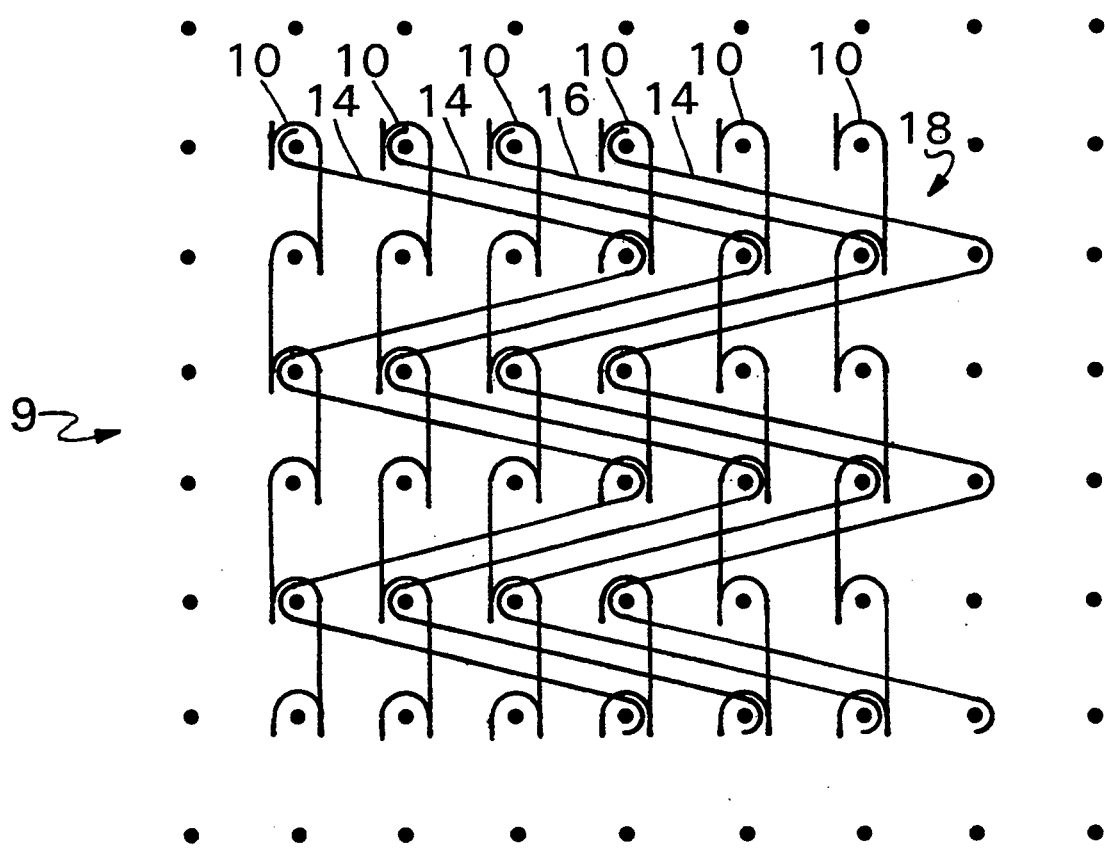
FIG. 3 is a stitch diagram combining the stitch diagrams of FIGS. 1 and 2.

As shown in FIG. 2, the fabric 9 is also comprised of a second group of a plurality of individual continuous multifilament fiberglass yarns 16, which may be identical to the first group of fiberglass yarns 10. However, the second group of yarns 16 is separately interspersed (i.e., in different loops of the lengthwise yarns 10) with a plurality of individual continuous thermoplastic yarns 14 forming a widthwise extending and lengthwise spaced-apart inlay 18. As shown in FIG. 3, the inlay 18 is interlaced with the lengthwise chains of spaced-apart fiberglass yarn loops 10.

The thermoplastic yarns 14 comprise from about 50% to about 100% of the individual yarns 14, 16 forming said inlay 18. Preferably, the inlay 18 comprises a ratio of two thermoplastic yarns 14 to one continuous multifilament fiberglass yarn 16 in the inlay 18. Therefore, the inlay 18 is preferably comprised of about 67% (two-thirds) thermoplastic yarns 14. Two thermoplastic yarns 14 should alternate with a single fiberglass yarn 16 forming the preferred pattern as illustrated in the stitch diagrams depicted in FIGS. 2 and 3.

The thermoplastic yarns 14 in the inlay 18 should have a melting point no greater than 400° F. Preferably the melting point is no greater than 300° F. The thermoplastic yarns 14 which are useful for the present fabric 9 include, for example, polyolefins, polyamide, polyester, acrylic, acetate, polyvinyl chloride and natural fiber blends thereof. Preferably, the thermoplastic yarn 14 used in the inlay 18 has a low melting point to avoid discoloration of the fabric 9 if it is heat bonded. While either textured or non-textured fibers may be used, the most preferred thermoplastic yarn 14 is 300 denier, 72 filament non-textured polypropylene yarn.

Figure 4:
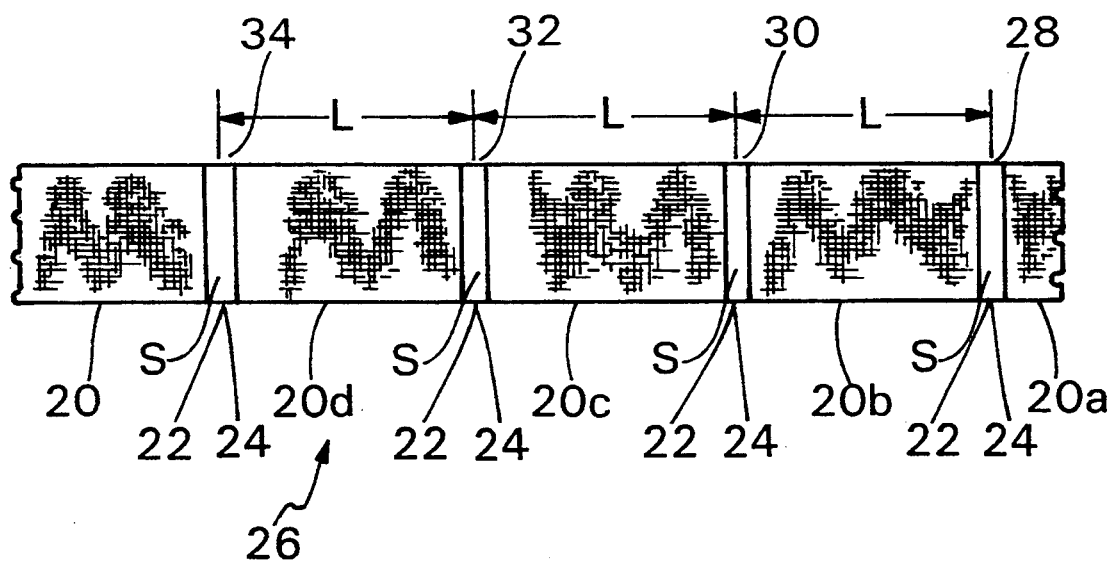
FIG. 4 is a schematic illustration showing the bonded areas for cutting a continuous length of the fabric of the present invention into bandages.

As seen in FIG. 4, the warp-knit casting fabric 9 is woven in a continuous length 26, such as disclosed in U.S. Pat. No. 4,745,912, and impregnated with resin by methods known to those skilled in the art. Generally, the fabric is resin-impregnated by coating with a polyisocyanate prepolymer composition. Preferably, the composition comprises modified diphenylmethane diisocyanate, polypropylene glycol, benzoyl chloride as a stabilizer, and a dimorpholinodiethylether catalyst. The benzoyl chloride preferably comprises from about 0.1 to 1.0% of the composition. The preferred ratio of the isocyanate to glycol reactive groups (NCO:OH) is about 4:1. In addition, foam suppressors such as silicone liquids may also be included. It will be understood by those skilled in the art that the fabric may be impregnated or coated with other resin compositions known to those skilled in the art. In addition, it will be understood that other common stabilizers or additives known to those skilled in the art may be substituted in the above described preferred composition without departing from the invention.

The resin-impregnated, warp-knit fabric 9 may then be used to make individual bandages 20 as shown in FIG. 4 having a leading edge 22 and a trailing edge 24 which retain desired flexibility and significantly resist raveling and fraying. It is understood by one skilled in the art that such bandages 20 are cut to size in accordance with their particular orthopedic application.

The thermoplastic yarns 14, due to their low melting point, well below that of the lengthwise and widthwise extending fiberglass yarns 10, 16, are suitable for forming a heat-activated bond to the fiberglass yarns 10, 16. The heat-activation forms a narrow bonded area or seal S, which may be made prior to or during cutting the continuous length 26 of fabric 9 into bandages 20, but preferably after the fabric has been resin-impregnated. The seal S should be about ⅛ inch measured along the longitudinal axis of the continuous length 26 of fabric 9 and should extend transversely from one side of the fabric 9 to the other side. The seal S may also be made by the application of ultrasonic energy.

In one embodiment, the continuous length 26 of fabric 9 is cut at pre-bonded positions 28, 30, 32, 34 to create leading and trailing edges 22, 24 by use of a heated apparatus such as a heated metal bar (not shown). An example of such an apparatus is a Sentinal heat sealer, available from Sentinal Machinery Division, Hyannis, Mass. It will be understood by one skilled in the art that any heated apparatus which will form a heat-activated bond between the thermoplastic yarns 14 and the fiberglass yarns 10, 16 is acceptable. A generally circular rolling knife assembly, similar to a "pizza cutter," is preferred in order to make a smooth cut through the heat bonded seal S. Another example of a useful cutting apparatus is the AZCO "Sur-Cut" knife cutter available from the AZCO Corporation, Elmwood Park, N.J. It will be understood by those skilled in the art that any cutting apparatus known in the art such as scissors, knives or scalpels for example may be used to cut the fabric.

Alternatively, a heated cutting apparatus may be employed to form the heat-activated seal S and to simultaneously cut the continuous length 26 of fabric 9 into bandages 20 of a desired length L at positions 28, 30, 32, 34. The length L varies in accordance with the length L required for any given orthopedic application. An example of a heated cutting apparatus includes the AZCO SC-125P heated knife cutter available from AZCO Corporation, Elmwood Park, N.J. It is understood by one skilled in the art that any heated cutting apparatus may be substituted without departing from the spirit of the present invention.

As an alternative to the formation of a heat-activated bond and seal S, ultrasonic energy may be used to bond and seal S the thermoplastic yarns 14 to the lengthwise and widthwise extending fiberglass yarns 10, 16. The ultrasonic energy is preferably provided by use of an ultrasonic horn "welder" (not shown) such as one manufactured by Sonobond Ultrasonics of West Chester, Pa. Another example of such an apparatus is the Branson Ultrasonic Sealer available from Branson Ultrasonics, Danbury, Conn. It is understood by those skilled in the art, that any apparatus may be used that provides ultrasonic energy such that a bond is formed between the thermoplastic yarns 14 and the fiberglass yarns 10, 16 at specified positions 28, 30, 32, 34 prior to cutting the continuous length 26 of fabric 9 at those positions to form individual bandages 20.

Cutting the fabric 9 may occur subsequent to or simultaneously with the application of ultrasonic energy in the same manner as described above with respect to the heat-activated bonding and cutting. Preferably, an ultrasonic horn "welder" described above is used which cuts and bonds the fabric simultaneously. However, any cutting tool which can simultaneously emit ultrasonic energy may be substituted without departing from the present invention.

The leading edge 22 of a bandage 20b (as well as the trailing edge 24 of the preceding bandage 20a) is formed by cutting the continuous length 26 of fabric 9, which has preferably first been impregnated with resin, in a direction transverse to the longitudinal axis of the continuous length 26 at a first position 28 where the thermoplastic yarns 14 are bonded to the lengthwise and widthwise extending fiberglass yarns 10, 16. The bond is formed and the cut is made as described above.

The trailing edge 24 of the same bandage 20b (as well as the leading edge 22 of the following bandage 20c) is formed by cutting the same continuous length 26 of fabric 9 in a transverse direction (generally parallel to the first cut) at a second position 30, spaced apart lengthwise at a distance L from the first position 28, where the thermoplastic yarns 14 are bonded to the lengthwise and widthwise extending fiberglass yarns 10, 16.

Additional bandages 20 may be made by continuing in the same manner as described above, for example, the trailing edge 24 of the bandage 20c (the leading edge 22 of a further bandage 20d) is formed by cutting the continuous length 26 of fabric 9 in a transverse direction (generally parallel to the first and second cuts) at a third position 32, spaced apart lengthwise at a distance L from the second position 30, where the thermoplastic yarns 14 are bonded to the lengthwise and widthwise extending fiberglass yarns 10, 16 (the leading edge 22 of the bandage 20c which is also the trailing edge 24 of bandage 20b is formed as described above). The trailing edge of the bandage 20d is then formed by cutting the continuous length 26 of fabric 9 in a like manner at a fourth position 34, a distance L from the third position 32, where the yarns are similarly bonded.

The present invention also comprises a method for forming resin-impregnated, warp-knit casting bandages 20 from the fabric 9 of the present invention. A continuous length 26 of the fabric 9, impregnated with resin is subjected to ultrasonic energy as previously described at predetermined positions 28, 30, 32, 34 to bond the thermoplastic yarns 14 to the widthwise and lengthwise extending continuous multifilament fiberglass yarns 10, 16. The continuous length 26 of fabric 9 is cut at the bonded positions 28, 30, 32, 34 each spaced a longitudinal distance L apart from the next consecutive position forming individual bandages 20 each having a leading edge 22 and a trailing edge 24 in a similar manner as described above for forming the bandages 20 by the application of heat. The ultrasonic energy may be applied simultaneously or prior to cutting the continuous length 26 of fabric 9 depending upon the type of apparatus providing the ultrasonic energy as described above.

The resulting bandages 20 which are ravel and fray resistant, substantially maintain the flexibility and strength of a 100% fiberglass fabric. The invention will now be described in more detail with respect to the following specific, non-limiting examples:

EXAMPLE I

A 3 inch wide warp knit fabric was prepared on a Raschel Knitting machine. The fabric comprised a warp of 100's fiberglass yarn (0.00025 inches in diameter with a strand count of approximately 100) and a fill of polypropylene multifilament yarn (300 denier, 72 filament) (Sample 1).

This fabric sample was coated with a polyisocyanate prepolymer comprising diphenylmethane diisocyanate, polypropylene glycol, benzoyl peroxide and dimorpholinodiethylether. A Control fabric sample was prepared on the same Raschel Knitting machine and coated with the same prepolymer. However, the Control contained a warp and fill of entirely 100's fiberglass yarn having the same specifications as the warp yarn of Sample 1.

The Control and Sample 1 were both individually subjected to a 400° F. sealing bar at a distance of 4 yards measured lengthwise (i.e., along the longitudinal axis) from the leading edge of each fabric piece forming a ½ inch lengthwise segment of stabilized coated web extending widthwise from one side to the other side of each piece of fabric. The Control and the Sample 1 were subsequently cut at the stabilized segments with a rolling knife assembly, and tested for cast setting time, exotherm, crush strength at 30 minutes, interlayer lamination and cut edge stability and appearance. The test results appear in Table I below.

TABLE I

|  | Sample 1 | Control |
| --- | --- | --- |
| Cast Setting Time (min.) | 3.75 | 3.50 |
| Exotherm (°F.) | 86 | 98 |
| Crush Strength at 30 min. (lbs.) | 88 | 109 |
| Interlayer Lamination (lbs.) | 54 | 46.5 |
| Cut Edge Stability | excellent | poor |
| Cut Edge Appearance | excellent | poor |

Overall the experimental Sample 1 was superior to the all fiberglass fabric Control in edge stability and appearance, but slightly weaker in cast strength as evidenced by the lower crush strength.

EXAMPLE 2

A 3 inch wide warp knit fabric was prepared on a Raschel Knitting machine. The fabric comprised a warp of 100's fiberglass yarn (0.00025 inches in diameter with a strand count of approximately 100) and a fill of 50% polypropylene multifilament yarn (300 denier, 72 filament) and 50% of the same fiberglass yarn as present in the warp. The polypropylene and the fiberglass yarns were individually alternated in the fill inlay (Sample 2).

This fabric was coated with the same prepolymer composition as that described in Example 1. Sample 2 was then subjected to a 400° F. heated sealing bar and cut by the same procedure set forth in Example 1. The cut edges were not well stabilized and were considered to be only slightly improved in appearance and stability when compared to the all fiberglass fabric Control sample of Example 1.

EXAMPLE 3

A 3 inch wide warp knit fabric was prepared on a Raschel Knitting machine. The fabric comprised a warp of 100's fiberglass yarns (0.00025 inches in diameter with a strand count of approximately 100) and a fill of two-thirds polypropylene multifilament yarn (300 denier, 72 filament) and one-third of the same fiberglass yarn as present in the warp (Sample 3). Two polypropylene yarns were alternated with each individual fiberglass yarn in the fill inlay.

Sample 3 was coated with prepolymer and then subjected to a 400° F. heated sealing bar and cut by the same procedure set forth in Example 1. Further, another 4 yard length of the above coated fabric was cut and sealed with an ultrasonic horn "welder" manufactured by Sonobond Ultrasonics, West Chester, Pa. (Sample 4). The two lengths of Samples 3 and 4 were then cut and tested in accordance with the tests outlined in Example 1. The results appear in Table II below.

TABLE II

|  | Sample 3 (rolling cut) | Sample 4 (ultrasonic) | Control |
| --- | --- | --- | --- |
| Cast Setting Time (min.) | 3.50 | 3.50 | 3.50 |
| Exotherm (°F.) | 95 | 95 | 98 |
| Crush Strength at 30 min. (lbs.) | 138 | 138 | 109 |
| Interlayer Lamination (lbs.) | 61 | 61 | 46.5 |
| Cut Edge Stability | excellent | excellent | poor |
| Cut Edge Appearance | excellent | excellent | poor |

As the results show, Samples 3 and 4, each having two polypropylene yarns alternated with each individual fiberglass yarn in the fill inlay, show an increased crush strength over the all fiberglass Control. The other properties of Samples 3 and 4 demonstrated by the test results are comparable to those of fiberglass. Significantly, Samples 3 and 4 demonstrate a substantial improvement in stability and appearance of their cut edges over the cut edges of the all fiberglass Control, thereby showing a high resistance to raveling and fraying.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A warp-knit casting bandage fabric, comprising:
   (a) a first group of a plurality of individual continuous multifilament fiberglass yarns forming lengthwise extending chains of spaced-apart loops; and
   (b) a second group of a plurality of individual continuous multifilament fiberglass yarns separately interspersed with a plurality of individual continuous thermoplastic yarns forming a widthwise extending and lengthwise spaced apart inlay interlaced with said lengthwise extending chains of spaced-apart loops such that the continuous thermoplastic yarns comprise from about 50% to about 100% of the total number of individual yarns forming said inlay and such that an open-knit construction is formed.

2. The warp-knit casting bandage fabric according to claim 1, wherein the continuous thermoplastic yarns comprise about 67% of the inlay.

3. The warp-knit casting bandage fabric according to claim 1, wherein every third individual yarn in the inlay is a continuous multifilament fiberglass yarn.

4. The warp-knit casting bandage fabric according to claim 1, wherein said fabric constitutes a single needle, two-bar warp-knit fabric.

5. The warp-knit casting bandage fabric according to claim 1, wherein said continuous multifilament fiberglass yarns have a diameter within the range of 0.00015 to 0.00036 inches and said fiberglass yarns have a strand count of 37 to 150.

6. The warp-knit casting bandage fabric according to claim 5, wherein said continuous multifilament fiberglass yarns have a diameter of about 0.00025 inches and a strand count of 100.

7. The warp-knit casting bandage fabric according to claim 1, wherein said continuous thermoplastic yarn has a melting point no greater than 400° F.

8. The warp-knit casting bandage fabric according to claim 7, wherein said continuous thermoplastic yarn has a melting point no greater than 300° F.

9. The warp-knit casting bandage fabric according to claim 1, wherein said continuous thermoplastic yarn is selected from the group consisting of polyolefin, polyamide, polyester, acrylic, acetate, polyvinyl chloride and natural fiber blends thereof.

10. The warp-knit casting bandage fabric according to claim 1, wherein said continuous thermoplastic yarn is 300 denier, 72 filament non-textured polypropylene yarn.

11. An elongated, resin-impregnated, warp-knit casting bandage, comprising:
   (a) a leading edge formed by cutting a resin-impregnated continuous length of the warp-knit casting bandage fabric of claim 1 in a direction transverse to the longitudinal axis of the bandage at a first position on the continuous length wherein the continuous thermoplastic yarns are bonded to the widthwise and the lengthwise extending continuous multifilament fiberglass yarns at the first position; and
   (b) a trailing edge formed by cutting the continuous length in a transverse direction at a second position spaced apart lengthwise from the first position wherein the continuous thermoplastic yarns are bonded to the widthwise and the lengthwise extending continuous multifilament fiberglass yarns at the second position.

12. The warp-knit casting bandage according to claim 11, wherein the bonds at the leading and the trailing edges are formed by subjecting the fabric to melting at the first position and at the second position prior to cutting the fabric at the first position and at the second position.

13. The warp-knit casting bandage according to claim 12, wherein the melting is creating by contacting the fabric with a hot metal bar.

14. The warp-knit casting bandage according to claim 11, wherein the bonds at the leading and the trailing edges are formed while simultaneously cutting the fabric at the first and second positions with a heated cutting apparatus.

15. The warp-knit casting bandage according to claim 11, wherein the bonds at the leading and the trailing edges are formed by subjecting the fabric to ultrasonic energy at the first position and at the second position prior to cutting the fabric at the first position and at the second position.

16. A method of forming an elongated, resin-impregnated, warp-knit casting bandage, comprising the steps of:
(a) subjecting a resin-impregnated, continuous length of the warp-knit casting fabric of claim 1 to ultrasonic energy at a first position on the continuous length wherein the thermoplastic yarns are bonded to the widthwise and the lengthwise extending continuous multifilament fiberglass yarns;
(b) cutting the continuous length at the first position in a direction transverse to the longitudinal axis of the continuous length of the fabric thereby forming a leading edge;
(c) subjecting the continuous length to ultrasonic energy at a second position spaced apart lengthwise from the first position such that the continuous thermoplastic yarns are bonded to the widthwise and the lengthwise extending continuous multifilament fiberglass yarns; and
(d) cutting the continuous length in a transverse direction at the second position thereby forming a trailing edge.

17. The method according to claim 16, wherein the ultrasonic energy is emitted from the cutting tool.

* * * * *